US005165388A

United States Patent [19]

Hartinger

[11] Patent Number: 5,165,388

[45] Date of Patent: Nov. 24, 1992

[54] ELECTRODYNAMIC SHOCKWAVE GENERATOR WITH A SUPERCONDUCTING COIL ARRANGEMENT

[75] Inventor: Benedikt Hartinger, Nuremberg, Fed. Rep. of Germany

[73] Assignee: Siemens Aktiengesellschaft, Munich, Fed. Rep. of Germany

[21] Appl. No.: 707,673

[22] Filed: May 30, 1991

[30] Foreign Application Priority Data

Jun. 13, 1990 [EP] European Pat. Off. ........... 90111220

[51] Int. Cl.[5] .............................................. A61B 17/22

[52] U.S. Cl. ............................ 128/24 OEL; 367/163; 367/174; 367/175

[58] Field of Search ....................... 128/24 EL, 660.03; 367/150, 157, 163, 165, 166, 174, 175; 174/15.5

[56] References Cited

U.S. PATENT DOCUMENTS

| | | | |
|---|---|---|---|
| 3,343,035 | 9/1967 | Garwin | 174/15.5 |
| 4,048,437 | 9/1977 | Vander Arend et al. | 174/15.5 |
| 4,333,228 | 6/1982 | Koch | 174/15.5 |
| 4,674,505 | 6/1987 | Pauli et al. . | |
| 4,766,888 | 8/1988 | Oppelt | 128/24 EL |
| 4,947,830 | 8/1990 | Rattner et al. . | |
| 5,057,645 | 10/1991 | Hilal | 174/15.5 |

FOREIGN PATENT DOCUMENTS

| | | | |
|---|---|---|---|
| 0209134 | 1/1987 | European Pat. Off. . | |
| 0298334 | 1/1989 | European Pat. Off. | 128/24 EL |
| 3737859 | 4/1989 | Fed. Rep. of Germany | 128/24 EL |
| 3742500 | 6/1989 | Fed. Rep. of Germany | 128/24 EL |

OTHER PUBLICATIONS

Japanese Application No. 56-138463, Patent Abstracts of Japan, vol. 7, No. 123 (E-178) [1268] (1983).

"Internally Cooled Cabled Superconductors" Hoenig, Cryogenics, vol. 22 No. 7 (1980) pp. 373-389.

*Primary Examiner*—Lee S. Cohen

*Assistant Examiner*—Krista M. Pfaffle

*Attorney, Agent, or Firm*—Hill, Van Santen, Steadman & Simpson

[57] ABSTRACT

An electrodynamic shockwave generator, of the type having a shockwave source formed by an electrically conductive membrane and an electrically driven coil, with the membrane being rapidly repulsed from the coil, causing the creation of a shockwave in an acoustic propagation medium disposed on one side of the membrane, upon the application of a pulse to the coil, wherein at least one of the coil or the membrane contains material which can be placed in a superconducting condition. A coolant, and a member for circulating the coolant are provided for placing the material in at least one of these electrically conductive elements in the superconducting condition.

13 Claims, 2 Drawing Sheets

ELECTRODYNAMIC SHOCKWAVE GENERATOR WITH A SUPERCONDUCTING COIL ARRANGEMENT

BACKGROUND OF THE INVENTION

1. Field of the Invention

The present invention is directed to an electrodynamically operated shockwave generator of the type having a shockwave source with an electrically conductive membrane an electrically driven coil, with shockwaves being generated in an acoustic propagation medium adjacent the membrane by rapid repulsion of the membrane from the coil when the coil is supplied with a high-energy pulse. The invention is more specifically directed to such a shockwave generator wherein one of the electrically conductive components of the shockwave source contains material which can be placed in a superconducting condition, and the shockwave generator includes means for placing the material in the superconducting condition.

2. Description of the Prior Art

Electrodynamic shockwave generators are known in the art which can be used for a variety of purposes, for example, in medicine for non-invasive fragmenting of calculi situated in the body of a patient, or for non-invasive treatment of pathological tissue conditions in a patient. Such shockwave generators can also be utilized for materials inspection, when such inspection requires charging the material with shockwaves. The shockwave generator is always acoustically coupled in a suitable manner to the subject which is to be acoustically irradiated, so that the shockwaves generated in the acoustic propagation medium, which is a part of the shockwave generator, can be transmitted into the subject. The shockwave generator and the subject to be acoustically irradiated must be aligned so that the region of the subject which is intended to be acoustically irradiated is situated in the propagation path of the shockwaves. If the shockwave generator generates focused shockwaves, it must also be assured that the region of the subject to be acoustically irradiated is situated in the focal region of the shockwaves.

A shockwave generator of this type is described in U.S. Pat. No. 4,674,505. This shockwave generator is a so-called electrodynamic or electromagnetic shockwave generator. In such a shockwave generator, the coil creates a magnetic field extremely rapidly by being charged with a high-voltage pulse. The magnetic field induces a current in the adjacent membrane which is opposite in direction to the direction of current flow through the coil. The membrane is thereby surrounded with a magnetic field having a field direction opposite to that of the magnetic field of the coil. As a consequence of the resulting repulsion forces, the membrane is rapidly moved away from the coil. A pressure pulse is thereby created in the acoustic propagation medium, which gradually steepens along its propagation path in the medium to form a shockwave. For simplicity, the phenomena which arises in the propagation medium will be always referred to herein as a shockwave, regardless of whether the pressure pulse has steepened to actually form a true shockwave.

A valid approximation for such shockwave generators is that the obtainable peak pressure of the shockwaves increases with the square of the current flowing through the coil. In practice, the coil in conventional shockwave generators must be charged with high-voltage pulses on the order of magnitude of 10 through 20 kV in order to elicit currents in the coil having a magnitude sufficient for generating shockwaves having the required peak pressure, after suitable focusing, for the fragmentation of calculi in the body of a patient. The necessity of having to charge the coil with voltages of this magnitude is considered highly disadvantageous in practice, because the insulating measures required for achieving an adequate electrical strength of the shockwave generator are problematical and extremely complex. Moreover, the high voltages have a disadvantageous effect not only on the surface life of the shockwave generator, but also on the electrical and electromechanical components of the high-voltage generator which is provided for driving the shockwave generator.

SUMMARY OF THE INVENTION

It is an object of the present invention to provide an electrodynamic shockwave generator wherein a high peak pressure of the shockwaves can be achieved when charging the coil arrangement or coil with electrical pulses having a relatively low voltage. It is to be understood that the term "coil" as used for the sake of simplicity hereinafter and in the appended claims is to comprise a coil arrangement of a plurality of coils as well as a single coil as in the case of described preferred embodiments.

The above object is achieved in accordance with the principles of the present invention in that at least one of the electrically conductive elements, i.e., the coil and/or the membrane, contains material which can be placed in the superconducting condition, and the shockwave generator includes means for placing that material in the superconducting condition. Because the ohmic resistance component of the coil and/or the membrane substantially disappears under such conditions, higher currents can flow in the coil and/or higher currents can be induced in the membrane because of the superconduction. This means that electrical pulses having a lower voltage, compared to the voltage required in conventional devices, are sufficient in such a shockwave generator to cause a defined current to flow in the coil. Alternativly, or additionally, a (further) reduction of the voltage of the electrical pulses is possible because higher repulsion forces occur as a consequence of the higher currents flowing in the membrane. In comparison to conventional devices, lower voltages are sufficient to generate shockwaves having a defined peak pressure. The coil and the electrical lines leading thereto in the shockwave generator constructed in accordance with the principles of the present invention are preferably designed with optimally low inductance, since the ohmic resistance component would otherwise represent only a small part of the overall impedance, and the elimination of the resistance component by superconduction would not yield a significant improvement.

In one embodiment of the invention, the coil can be placed in the superconducting condition with a coolant situated in the region of the coil. Because the coil must usually be fixed to a coil carrier, the coil carrier can be provided with a channel through which the coolant flows optimally close to the coil. In a preferred version, the coil is formed by a wound tube consisting of material which can be placed in the superconducting condition, and the coolant flows through the tube. This permits the coil to be placed in the superconducting condition with particularly low structural outlay, since a separate channel system or the like is not required to bring the coolant to the coil.

In a further embodiment of the invention, coolant is used to place the membrane in the superconducting condition, with the coolant also functioning as the acoustic propagation medium. The coolant is contained in a space adjacent the membrane. Since the coolant places the membrane in the superconducting condition and also serves as the acoustic propagation medium for the shockwaves, and since such an acoustic propagation medium must be present in any event, no additional structural outlay is required to place the membrane in the superconducting condition. In a version of this embodiment, the volume in which the coolant is contained has an end remote from the membrane terminated with a solid plate consisting of material which conducts shockwaves, i.e., a material having a low acoustic attenuation for shockwaves. That side of the solid plate facing away from the membrane adjoins a second volume, wherein a medium which conducts shockwaves, and whose temperature is higher than the temperature of the coolant, is contained. This version is of particular significance if the membrane consists of a material requiring extremely low temperatures, i.e., temperatures significantly below 170° K., for reaching the superconducting condition, because non-extreme temperatures, for example, on the order of magnitude of ordinary room temperature, can be present on the other side of the solid plate, as "seen" from the membrane. Dependent on the thickness of the solid plate, the heat transfer from the medium which conducts the shockwaves through the solid plate into the coolant can be influenced, because the heat transfer will become lower as the thickness of the solid plate increases.

In order to introduce the shockwaves into a subject to be acoustically irradiated with low acoustic losses, it may be necessary, for example, if the acoustic impedance of the medium contained in the aforementioned second volume deviates substantially from the acoustic impedance of the subject, to provide a partition consisting of material which conducts shockwaves at a location terminating the second volume at its end remote from the solid plate. A substance having an acoustic impedance substantially corresponding to that of the subject can then be disposed adjoining that side of the partition facing away from the second volume.

If the shockwaves emanating from the membrane require focusing, in a further embodiment of the invention the partition may be fashioned as an acoustic lens. Thus, if both a partition and an acoustic lens are required, the necessary structural outlay can be considerably reduced. When calculating the curvature of the lens, the changes in the refractive index of the lens material, caused by a temperature gradient which may exist in the lens material transversely relative to the propagation direction of the shockwaves, can be taken into consideration.

In a further embodiment of the invention a flexible sack for acoustic application of the shockwave generator to a patient to be acoustically irradiated is provided. The sack may in the form of bellows, with material which conducts shockwaves being contained inside the bellows, and the temperature of this material being substantially the same as the body temperature of the patient. Depending on the temperature at which the membrane material converts into the superconducting condition, the material contained within the bellows can be coolant disposed in the volume preceding the membrane, or may be the medium contained in the second volume, or may be the substance which adjoins the partition at the side thereof facing away from the second volume, or may be a special material.

It will be understood that the acoustic impedances of these substances situated in the propagation path of the shockwaves should only minimally differ from the acoustic impedance of the subject to be acoustically irradiated, in order to avoid reflection losses as much as possible.

DESCRIPTION OF THE PREFERRED EMBODIMENTS

Figure 1:
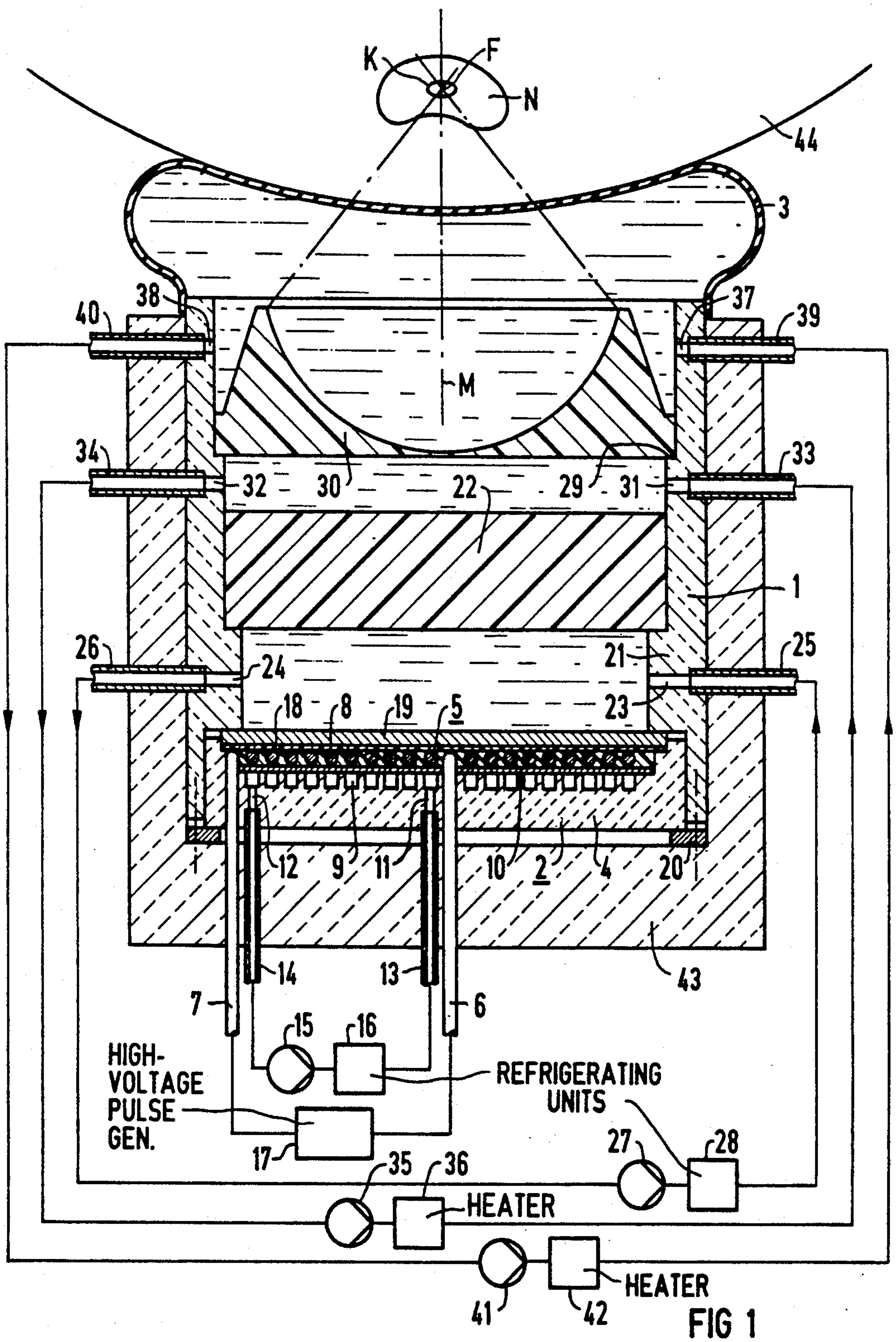
FIG. 1 is a longitudinal sectional view through a shockwave generator constructed in accordance with the principles of the present invention, with components for operating the shockwave generator being schematically shown.

A shockwave generator constructed in accordance with the principles of the present invention, of the type suitable for fragmenting calculi, is shown in FIG. 1. The shockwave generator has a tubular housing 1, with one end closed by a shockwave source generally referenced 2, and an opposite end closed by a flexible sack 3.

The shockwave source 2 includes a coil 5 arranged in a planar seating surface of a coil carrier 4. The coil 5 has terminals 6 and 7, with a plurality of spiral turns (one of the turns being referenced 8) being disposed between the terminals 6 and 7. The coil carrier 4 consists of an electrically insulating material, for example, aluminum oxide ceramic. The space between the individual turns 8 of the coil 5 is filled with an electrically insulating casting resin, for example, Araldit ®. The coil 5 consists of a material which can be placed in the superconducting condition, for example, yttrium-barium-copper oxide, which remains superconducting to temperatures of approximately 90° K. To place the coil 5 in the superconducting condition, a spiral groove 9 is provided in the coil carrier 4, the groove 9 being closed fluid-tight with a disc 10 consisting of the same material as the coil carrier 4. A channel having an inlet opening 11 and an outlet opening 12 is thereby formed. An inlet line 13 and an outlet line 14 are connected to this channel. Liquid nitrogen, whose temperature of 77° K. is sufficient to place the material of the coil 5 in the superconducting condition, is pumped through the channel as coolant, by means of a pump 15. A refrigeration unit 16 is provided to assure that the nitrogen remains in its liquid condition. The terminals 6 and 7 of the coil 5 are connected to an electrical pulse generator 17.

A planar membrane 19, in the shape of a circular disc, is disposed opposite that side of the coil 5 facing away from the carrier 4. An insulating foil 18 is disposed between the coil 5 and the membrane 19. The membrane 19 is also composed of a material which can be placed in the superconducting condition, for example, barium-lanthanum-copper oxide. The membrane 19, the insulating foil 18 and the coil 5 are combined in a unit with the coil carrier 4 and the disc 10. The coil carrier 4 has stepped interior edges to receive and center these components. This unit is pressed against a shoulder 21, provided in the bore of the housing 1, by a ring 20 adjoining the coil carrier 4 and by several screws (only the respective center lines of two of the screws being indicated in FIG. 1 with dot-dashed lines). The membrane 19 thereby is maintained liquid-tight against the shoulder 21. A suitable sealing means (not shown) may be interposed between the membrane 19 and the shoulder 21.

A solid plate 22, consisting of material having a low thermal conductivity, for example polystyrol, presses fluid-tight against that side of the shoulder 21 facing away from the membrane 19. Liquid nitrogen, whose presence places the membrane 19 in the superconducting condition, is contained in the space defined by the solid plate 22 and the membrane 19. This space has an inlet 23 and an outlet 24, to which an inlet line 25 and outlet line 26 are respectively connected, so that the liquid nitrogen can be circulated as coolant with a pump 27. A further refrigerating unit 28 is again provided to maintain the nitrogen in its liquid condition.

A plano-concave acoustic positive lens 30, which may consist of polystyrol, is mounted on a further shoulder 29 of the bore of the housing 1. The planar side of the positive lens 30, facing toward the solid plate 22, and that side of the solid plate 22 facing toward the planar side of the positive lens 30 define a further space wherein a liquid is situated which functions as a medium for conducting shockwaves. The temperature of this liquid does not significantly deviate from the normal ambient temperatures, i.e., approximately 20° through 30° C. Glycerin may, for example, be used as this liquid, since glycerin has an acoustic impedance similar to that of polystyrol. Because a defined amount of heat will flow from this fluid through the solid plate 22 into the liquid nitrogen adjacent the membrane 19, the fluid contained between the positive lens 30 and the solid plate 22 is conducted via a pump 35 through a heater 36 via an inlet line 33 connected to an inlet 31, and an outlet line 33 connected to an outlet 32. The heater 36 compensates for heat losses and insures that the liquid will be maintained at a constant temperature using known thermostatic control techniques.

The space between the positive lens 30 and the sack 3 is filled with a further liquid, for example water, having an acoustic impedance matched as precisely as possible to that of the tissue of the patient to be treated. This further liquid material is circulated with a pump 41 via an inlet 37 connected to an inlet line 39 and an outlet 38 connected to an outlet line 40. The further liquid is held at a constant temperature with a thermostat-controlled heater 42, so that the temperature of the further liquid does not significantly deviate from the body temperature of the patient to be treated.

Shockwaves are generated in a known manner in the shockwave generator disclosed herein by charging the coil 5 with a voltage pulse generated by the pulse generator 17. In response thereto, the coil 5 constructs a magnetic field extremely rapidly, which induces a current in the membrane 19 in an opposite direction to the current flowing through the coil 5. The membrane current generates a magnetic filed in a direction opposite to the magnetic field associated with the current flowing through the coil 5. As a consequence of the repulsion forces, the membrane 19 is moved suddenly away from the coil 5. This causes an initially planar shockwave to be introduced into the acoustic propagation medium adjoining the membrane 19, i.e., into the liquid nitrogen in the case of the shockwave generator disclosed herein.

In contrast to conventional devices, significantly lower voltages are required in the shockwave generator disclosed herein for generating a shockwave having a defined energy content and a defined peak pressure, because of one of or both the coil 5 and the membrane 19 being in the superconducting condition. This is because, assuming a low-inductance structure of the shockwave generator, relatively low voltages are sufficient to cause the required currents to flow, because the ohmic resistance component of the coil 5 has been substantially eliminated. Secondly, due to the substantial elimination of the ohmic resistance component of the membrane 19, higher currents can be induced therein, which in turn result in higher repulsion forces, so that a further reduction in the voltage with which the coil 5 is to be charged is possible.

In the shockwave generator of FIG. 1, the liquid nitrogen which is situated between the membrane 19 and the solid plate 22, and which places the membrane 19 in the superconducting condition, simultaneously serves as an acoustic propagation medium for the shockwaves emanating from the membrane 19. The shockwaves pass through the solid plate 22 as well as through the liquid situated between the solid plate 22 and the planar side of the positive lens 30. The substantially planar shockwave entering into the positive lens 30 is focused onto a focal region F as a consequence of the action of the positive lens 30, as indicated with dot-dashed lines. The focal region F lies on a center axis M of the shockwave source. When the sack 3 of the shockwave generator, with the assistance of a known, suitable locating system, is pressed against the body 44 of a patient to be treated in such a position that the calculus K to be fragmented, for example a kidney stone N, is situated in the focal region F, the calculus K can be broken into fragments with a series of shockwaves. The fragments are so small that they can be eliminated naturally.

The solid plate 22, which as mentioned above consists of a material having low thermal conductivity, serves the purpose of maintaining the quantity of heat supplied per time unit to the liquid nitrogen situated between the solid plate 22 and the membrane 19 as low as possible. For the same reason, a schematically indicated heat insulator 43 is provided, which surrounds the entire housing 1, with the exception of the end closed by the sack 3. The heat insulator 43 may be an element consisting of a suitable insulating material, for example Styropor ®, or may be an evacuated, double-walled element, or both. The heat insulator 43 also prevents ambient heat from being supplied to the liquid nitrogen situated in the region of the coil 5 in the channel formed by the groove 9 and the disc 10.

The liquid situated between the solid plate 22 and the positive lens 30 serves the purpose of maintaining the extreme temperatures of the liquid nitrogen away from the subject to be acoustically irradiated, i.e., away from the body 44 of the patient to be treated, and also produces physiologically comfortable temperatures at the region of that end of the shockwave generator in engagement with the body 44.

Further temperature matching is achieved with the liquid enclosed between the positive lens 30 and the sack 3, which also serves the purpose of acoustic impedance matching to the conditions of the body 44 of the patient to be treated. Particularly if human patients are to be treated, it is recommended to provide water as the liquid between the sack 3 and the positive lens 30, since the acoustic impedance of water corresponds almost exactly to that of human body tissue.

It is preferred that the substances or materials respectively comprising the solid plate 22, the positive lens 30, the liquid between the membrane 19 and the solid plate 22, and the liquid between the solid plate 22 and the positive lens 30, be selected to have material properties such that acoustic losses in the propagation direction of the shockwaves, due to reflections and attenuation, are maintained within limits. For example, the respective acoustic impedances of the various substances should not substantially differ from one another so as to maintain the reflection losses low. If liquid argon (acoustic impedance=$1.1075\times10^3$ kg/m$^2$s) is used as the liquid between the membrane 19 and the solid plate 22, polystyrol (acoustic impedance=$2.800\times10^3$ kg/m$^2$s) is used as the material for the solid plate 22 and for the positive lens 30, and glycerin (acoustic impedance=$2.420\times10^3$ kg/m$^2$s) is used as the liquid between the solid plate 22 and the lens 30, the losses are comparable to those of conventionally constructed shockwave generators having water as the acoustic propagation medium for the entire volume between the membrane and the sack. As further progress is made in the field of high-temperature superconduction, it is expected that oils, glycerins, alcohols, etc., may be used in future embodiments as the liquids between the membrane 19 and the solid plate 22. Under certain circumstances, this would enable a further improvement in the acoustic matching, and thus a further reduction in acoustic losses.

Figure 2:
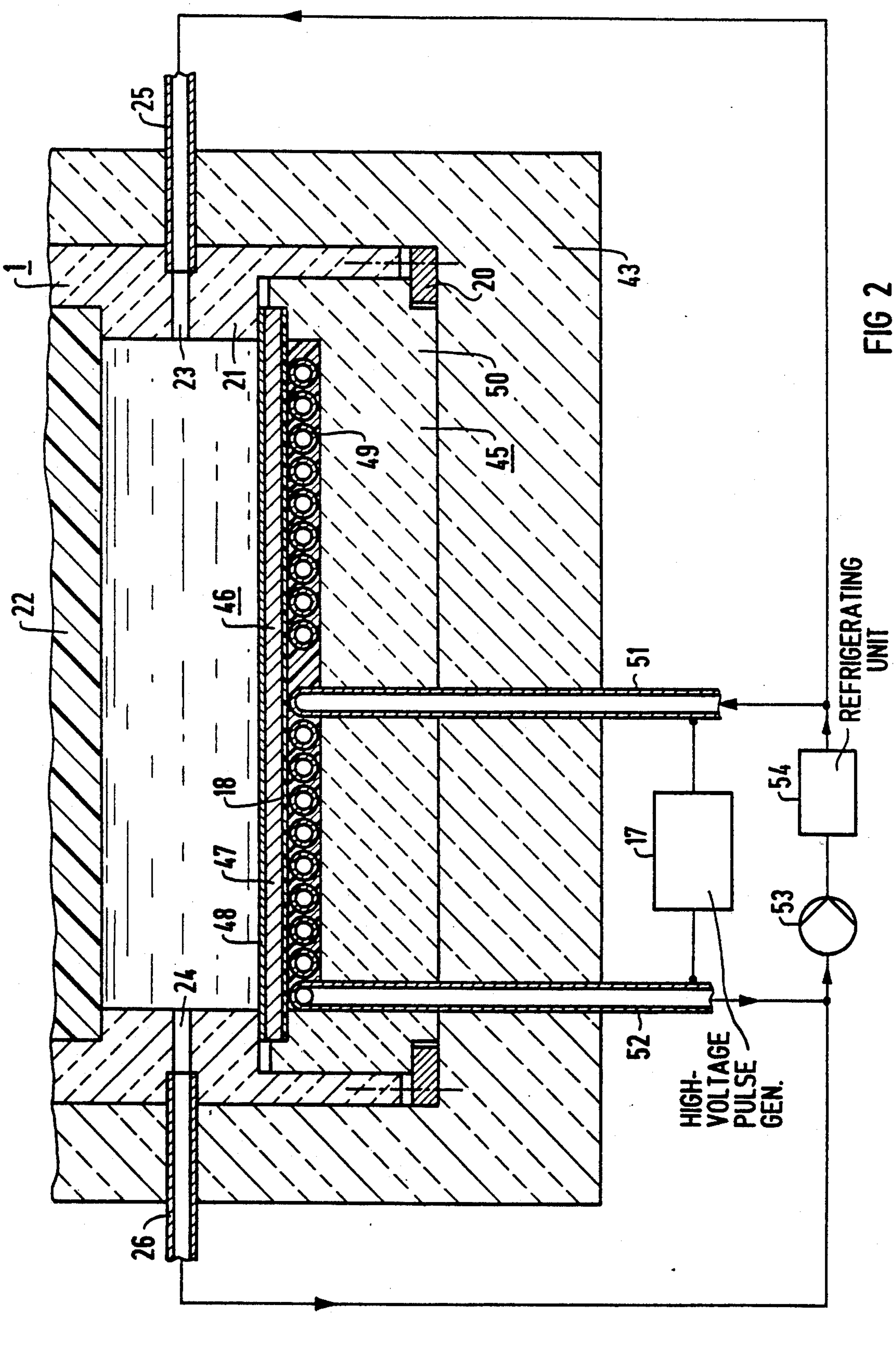
FIG. 2 is longitudinal section through a portion of a further embodiment of a shockwave generator constructed in accordance with the principles of the present invention, with components for operating the shockwave generator being schematically shown.

A further embodiment of a shockwave generator constructed in accordance with the principles of the present invention is shown in FIG. 2. Only that portion of the shockwave generator containing the shockwave source, generally referenced 45, is shown in FIG. 2. Components thereof already identified and described in connection with FIG. 1 have the same reference symbols.

In contrast to the exemplary embodiment described above, wherein the membrane 19 consists completely of material which can be placed in the superconducting condition, the membrane 46 in the shockwave source 45 in FIG. 2 is formed by a carrier 48, which may, for example, consist of titanium, and a layer 47 attached to the carrier 48 consisting of a material which can be placed in the superconducting condition, for example, barium-lanthanum-copper oxide The carrier 48 serves as to mechanically fix and stiffen the layer 47, in which high currents can be induced since it is adjacent to the coil 49.

The coil 49 is arranged on the planar seating surface of a coil carrier 50, and is in the form of a spiral. In contrast to the embodiments of FIG. 1, the coil 49 in the embodiment of FIG. 2 is fabricated of a tube of material which can be placed in the superconducting condition, for example barium-lanthanum-copper oxide. The liquid nitrogen which places this material in the superconducting condition flows through the interior of the tube forming the coil 49. It is thus not necessary to provide a separate channel system in the coil carrier 50 to bring the liquid nitrogen into the region of the coil 49. The coil 49 has two terminals 51 and 52 by which it is connected to the pulse generator 17. The terminals 51 and 52 simultaneously respectively serve as an inlet and outlet for the liquid nitrogen, and consequently are connected to a pump 53 and to a refrigerating unit 54. The pump 53 and the refrigerating unit 54 are also responsible for the liquid nitrogen situated between the membrane 46 and the solid plate 22, and therefore inlet line 25 and the outlet line 26 are also connected to the pump 53 and to the refrigerating unit 54.

The exemplary embodiments described above have been directed to shockwave generators of the employed for the fragmentation of calculi. The inventive principles disclosed herein, however, can be used in shockwave generators which are used for other purposes. Also, in the above embodiments both the membrane and the coil have been shown as being substantially planar. Shockwave generators embodying the inventive principles can, however, alternatively be constructed wherein the membrane and the coil do not have a planar configuration, but may, for example, be spherically curved around a common center.

In the above embodiments, high-temperature superconductors, namely yttrium-barium-copper oxide and barium-lanthanum-copper oxide, have been disclosed as examples of the material contained in the coil and in the membrane which can be placed in the superconducting condition. Of course, other high-temperature superconductors may be used, and substances other than liquid nitrogen may be used to place these materials into the superconducting condition.

Although other modifications and changes may be suggested by those skilled in the art, it is the intention of the inventor to embody within the patent warranted hereon all changes and modifications as reasonably and properly come within the scope of his contribution to the art.

I claim as my invention:

1. An electrodynamic shockwave generator comprising:

a housing;

a shockwave propagation medium contained in said housing;

electrodynamic means in said housing for generating shockwaves in said shockwave propagation medium, including an electrically conductive coil connected to a high-voltage pulse generator and an electrically conductive membrane disposed between said coil and said shockwave propagation medium, said membrane being rapidly repelled by said coil upon the application of a high-voltage pulse to said coil to generate said shockwaves in said shockwave propagation medium, said coil and said membrane constituting electrically conductive components;

at least one of said electrically conductive components containing material which can be placed in a superconducting condition; and means in thermal contact with said at least one electrically conductive component for placing said material in said at least one electrically conductive component in said superconducting condition.

2. A shockwave generator as claimed in claim 1 wherein said coil consists of material which can be placed in a superconducting condition, and wherein said means in thermal contact is a coolant situated in the region of said coil which places said material in said superconducting condition.

3. A shockwave generator as claimed in claim 2 further comprising: a coil carrier to which said coil is fixed, said coil carrier having a channel therein, forming a part of said means in thermal contact, and wherein said means in thermal contact includes means for circulating said coolant through said channel past said coil.

4. A shockwave generator as claimed in claim 1 wherein said coil consists of a spirally wound tube consisting of material which can be placed in the superconducting condition, and wherein said means in thermal contact comprises a coolant, and means for circulating said coolant through the interior of said tube to place said material in said superconducting condition.

5. A shockwave generator as claimed in claim 1 wherein said membrane contains material which can be placed in a superconducting condition, wherein said shockwave propagation medium is a coolant, and wherein said coolant is disposed in a defined volume within said housing adjacent said membrane for placing said material in said membrane in said superconducting condition.

6. A shockwave generator as claimed in claim 5 wherein said defined volume is limited on one side by said membrane and is limited on an opposite side by a solid plate consisting of shockwave propagation material, and said housing containing a further volume, limited on one side by an opposite side of said solid plate facing away from said membrane, and said shockwave generator further comprising a further shockwave propagation medium contained in said further volume, said further shockwave propagation medium being at a temperture higher than the temperature of said coolant.

7. A shockwave generator as claimed in claim 6 further comprising a partition limiting an opposite side of said further volume, said partition consisting of shockwave propagating material, and said shockwave generator further comprising another volume in said housing, limited on one side by said partition, and containing a substance having an acoustic impedance substantially corresponding to the acoustic impedance of a subject to be acoustically irradiated by said shockwave generator.

8. A shockwave generator as claimed in claim 7 further comprising a flexible sack limiting an opposite side of said another volume for acoustically applying said shockwave generator to said subject, and wherein said substance in said another volume has a temperature substantially the same as a body temperature of said subject.

9. A shockwave generator as claimed in claim 7 wherein said partition is an acoustic lens for focusing said shockwaves.

10. A shockwave generator as claimed in claim 1 wherein said means in thermal contact is a coolant, and means for circulating said coolant sufficiently close to said at least one electrically conductive component for placing said material in said at least one electrically conducting component in said superconducting condition.

11. A shockwave generator as claimed in claim 1 wherein said membrane consists of a carrier layer comprised of non-superconducting material and an electrically conductive layer, disposed adjacent said carrier layer, consisting of said material which can be placed in the superconducting condition.

12. An electrodynamic shockwave generator comprising:
- a housing;
- a shockwave propagation medium contained in said housing;
- electrodynamic means in said housing for generating shockwaves in said shockwave electrodynamic medium, including an electrically conductive coil connected to a high-voltage pulse generator and an electrically conductive membrane disposed between said coil and said shockwave propagation medium, said membrane being rapidly repelled by said coil upon the application of a high-voltage pulse to said coil to generate said shockwave in said shockwave propagation medium;
- said coil being formed by a spirally wound tube consisting of material which can be placed in a superconducting condition; and
- a coolant, and means for circulating said coolant through the interior of said tube to place said material comprising said tube in said superconducting condition.

13. A electrodynamic shockwave generator comprising:
- a housing;
- a shockwave propagation medium contained in said housing;
- electrodynamic means in said housing for generating shockwaves in said shockwave electrodynamic medium, including an electrically conductive coil connected to a high-voltage pulse generator and an electrically conductive membrane disposed between said coil and said shockwave propagation medium, said membrane being rapidly repelled by said coil upon the application of a high-voltage pulse to said coil to generate said shockwave, in said shockwave propagation medium;
- said membrane containing material which can be placed in a superconducting condition;
- said shockwave propagation medium consisting of coolant and being contained in a defined volume with said coolant in thermal contact with said membrane; and
- means for circulating said coolant through said volume to place said material in said membrane in said superconducting condition.

* * * * *